United States Patent
Litkouhi et al.

(10) Patent No.: US 6,749,599 B2
(45) Date of Patent: Jun. 15, 2004

(54) APPARATUS AND METHOD FOR REMOVING A LODGED MASS FROM AN ANIMAL AIRWAY

(76) Inventors: Bahman Litkouhi, 860 Roslyn Rd., Ridgewood, NJ (US) 07450; James T. DeLuca, 15 Wendover Rd., Forest Hills Garden, NY (US) 11375; Robert H. Abplanalp, Ten Hewitt Ave., Bronxville, NY (US) 10708

( * ) Notice: Subject to any disclaimer, the term of this patent is extended or adjusted under 35 U.S.C. 154(b) by 0 days.

(21) Appl. No.: 10/251,328

(22) Filed: Sep. 20, 2002

(65) Prior Publication Data

US 2003/0028158 A1 Feb. 6, 2003

Related U.S. Application Data

(62) Division of application No. 08/888,581, filed on Jul. 7, 1997, now Pat. No. 6,478,770.

(51) Int. Cl.[7] .............................................. A61M 31/00
(52) U.S. Cl. ........................................ 604/514; 604/500
(58) Field of Search ...................... 128/207.17, 207.14, 128/207.15, 207.18, 911, 912, DIG. 26; 604/174, 514, 180, 500

(56) References Cited

U.S. PATENT DOCUMENTS 4,579,114 A * 4/1986 Gray et al. ............ 128/203.11
4,790,818 A * 12/1988 DeLuca et al. ............... 604/54

* cited by examiner

*Primary Examiner*—Manuel Mendez
(74) *Attorney, Agent, or Firm*—Kilgannon & Steidl

(57) ABSTRACT

An apparatus and method for removing a lodged mass from an airway of a human or animal in which the source of suction is a sealed vacuum container which is punctured when the device is positioned within the mouth of the victim. As contrasted with prior art devices of this type, the retracting force created due to the pressure differential is developed instantaneously to a greater degree than heretofore obtainable, and this force is maintained until the foreign object is completely dislodged.

6 Claims, 7 Drawing Sheets

APPARATUS AND METHOD FOR REMOVING A LODGED MASS FROM AN ANIMAL AIRWAY

This application is a divisional of U.S. patent application Ser. No. 08/888,581, filed Jul. 7, 1997, now U.S. Pat. No. 6,478,770.

BACKGROUND OF THE INVENTION

This invention relates generally to the field of surgical instrumentation and procedure, and more particularly to an improved device and procedure for removing obstructions, usually large particles of food, which have accidentally become lodged in the animal airway to cause choking.

A common cause of choking or obstruction of the human airway is from food or other foreign objects lodged in the back of the throat above or below the epiglottis. If the obstruction is not removed promptly from the airway of the victim, death due to suffocation can occur in a matter of a few minutes.

In common manual emergency techniques, such as back slapping (back blows), chest thrust, or the Heimlich maneuver, the back blows, or the compressions of the chest or the diaphragm, are to cause the pressure inside the lungs to increase to a value greater than the atmospheric pressure which exists above the lodged bolus in the mouth cavity. The difference in pressure between the two sides of the bolus causes an upward force acting on the bolus. This force, if large enough, should overcome the restricting forces that are produced by the throat wall.

Even though these manual techniques have saved many lives, they are not always effective and each one has its deficiencies. For instance, back slapping may further complicate the situation by causing a partial obstruction to become a complete blockage or the Heimlich maneuver, which since 1985 has been recommended by the Surgeon General as the most effective method that should be used on choking victims, if performed incorrectly, may result in fractured ribs or damaged internal organs. Furthermore, the prior art literature indicates that pressure differential created by these methods is on the order of 0.5 psi. This pressure differential is often insufficient for the removal of a tightly lodged object.

In addition to the manual techniques referred to above, a number of mechanical devices for the removal of the lodged bolus from the airway of the choking victim have been patented. In this approach, a pressure difference between the two sides of the bolus is created by lowering the pressure inside the mouth cavity (above the bolus) to a pressure less than the pressure in the lungs. Prior mechanical devices are described in U.S. Pat. Nos. 3,946,736 (Neward), 4,662,367 (Gore), 4,790,818 (DeLuca) and 4,971,053 (Tarrats).

In general, there are at least four conditions that are considered essential to maximize the chance for the successful removal of an obstructing object from the airway of the victim.

1. The upward force created due to the pressure differential across the obstructing object must be large enough to overcome the frictional forces between the object and the area of lodgement.
2. The applied pressure difference should be retained until the object is completely dislodged, i.e. an initial high pressure differential pulse alone may not be sufficient for the removal of the object.
3. The creation of the initial high pressure differential across the object should be sudden and instantaneous, i.e. a gradual build up of the pressure differential is not favored.
4. Since the pressure differential is created by the evacuation of the mouth cavity (mechanical device applications), the device must seal about the mouth and the nostril of the victim.

As mentioned earlier, in the case of the back slapping and Heimlich techniques, the created pressure differential is of the order of 0.5 psi. Furthermore, in these techniques, the duration of the applied pressure differential is relatively short.

Neward's device, called Throat-E-Vac, comprises a hand operating vacuum pump, a mouthpiece, a hollow tongue depressor, and a nose clamp. This device is capable of creating a high pressure differential and meets conditions 2 and 4, however, it does not meet condition 3, for reason that the creation of the vacuum is gradual instead of being instantaneous.

Gore's invention comprises a tube-like device that is inserted in the victim's throat enclosing the larynx area at one end, while the rescuer sucks on the other end in an attempt to remove the lodged bolus. A filter is also provided within the tube to absorb the liquid flowing through the tube. This device poorly meets conditions 1, 2 and 3.

DeLuca's invention comprises a hollow tongue depressor element, a high pressurized air canister, a manually activated valve and a jet tube orifice placed within an outer tube shell. This device is based on the principle of indirect suction, i.e., by positioning the free end of the tongue depressor in the throat of the victim and opening the valve, a sudden jet of air shoots out from the canister through the jet tube orifice. This jet stream causes a secondary flow through the tube shell resulting in creating a vacuum within the mouth cavity. Even though this device is capable of creating a relatively high pressure differential in a short period of time, it does not meet conditions 2 and 4.

Tarrats' invention comprises a piston-cylinder mechanism loaded with a spring, a mask and an airway tube which extends from the mask into the victim's mouth. The principle of operation of this device is very similar to that of Neward's device, namely, like Neward's hand-operating vacuum pump, this device also uses a piston and cylinder arrangement for creating of vacuum. Tarrats' device, however, seems heavier and mechanically more complex and difficult to operate.

SUMMARY OF INVENTION

Briefly stated, the invention is an apparatus and method for dislodging an article, be it a bolus or other mass, from an animal breathing passage. This apparatus comprises a puncturable, pre-evacuated canister, a release valve, a mask which seals the victim's oral and nasal cavities, a hollow tongue depressor, the mask being mounted on the tongue depressor and non-collapsible conduit means for connecting the canister and the mask to the release valve.

The method of the subject invention involves instantly exposing the oral cavity through valved conduit means to a vacuum reservoir. This, in contrast to systems wherein a lowered pressure is developed in the oral cavity through a venturi created vacuum or a vacuum pump.

In the method of this invention the free end of the tongue depressor is disposed in the throat of the victim and with the mask in sealing position over the victim's oral and nasal cavities, the evacuated canister is punctured. The release valve is then opened to thereby communicate the interior of the canister and the oral cavity of the victim to effect an instantaneous vacuum within the oral cavity. The vacuum condition is sustained in the oral cavity until the bolus or other undesired mass is completely dislodged. For the method of this invention, it is not critical that the free end of the tongue depressor be first placed in the mouth of the victim. The order of steps may be reversed and the evacuated canister first punctured and then the tongue depressor placed into the oral cavity with the mask sealing the nasal and oral cavity.

What is important is that the release valve allowing the communication of the oral cavity and the evacuated canister not be opened until the apparatus is placed in a sealing position against the nasal and oral cavities. Moreover, it is important in carrying out the method of the invention that the nasal and oral cavities be effectively sealed in order to maximize the pressure differential on each side of the bolus or lodged object in the throat cavity.

It should also be mentioned that, for many of the above-described prior art systems, the vacuum is created at the site, while, as will be described more fully in the next section, in the invention presented here, the vacuum is brought ready to the site. This not only shortens the operating time, but also eliminates the need for having many of the above-mentioned mechanical parts, such as a piston, cylinder, spring, orifice, hand pump, etc., needed for the creation of the vacuum at the site.

DETAILED DESCRIPTION OF THE INVENTION

Figure 1:
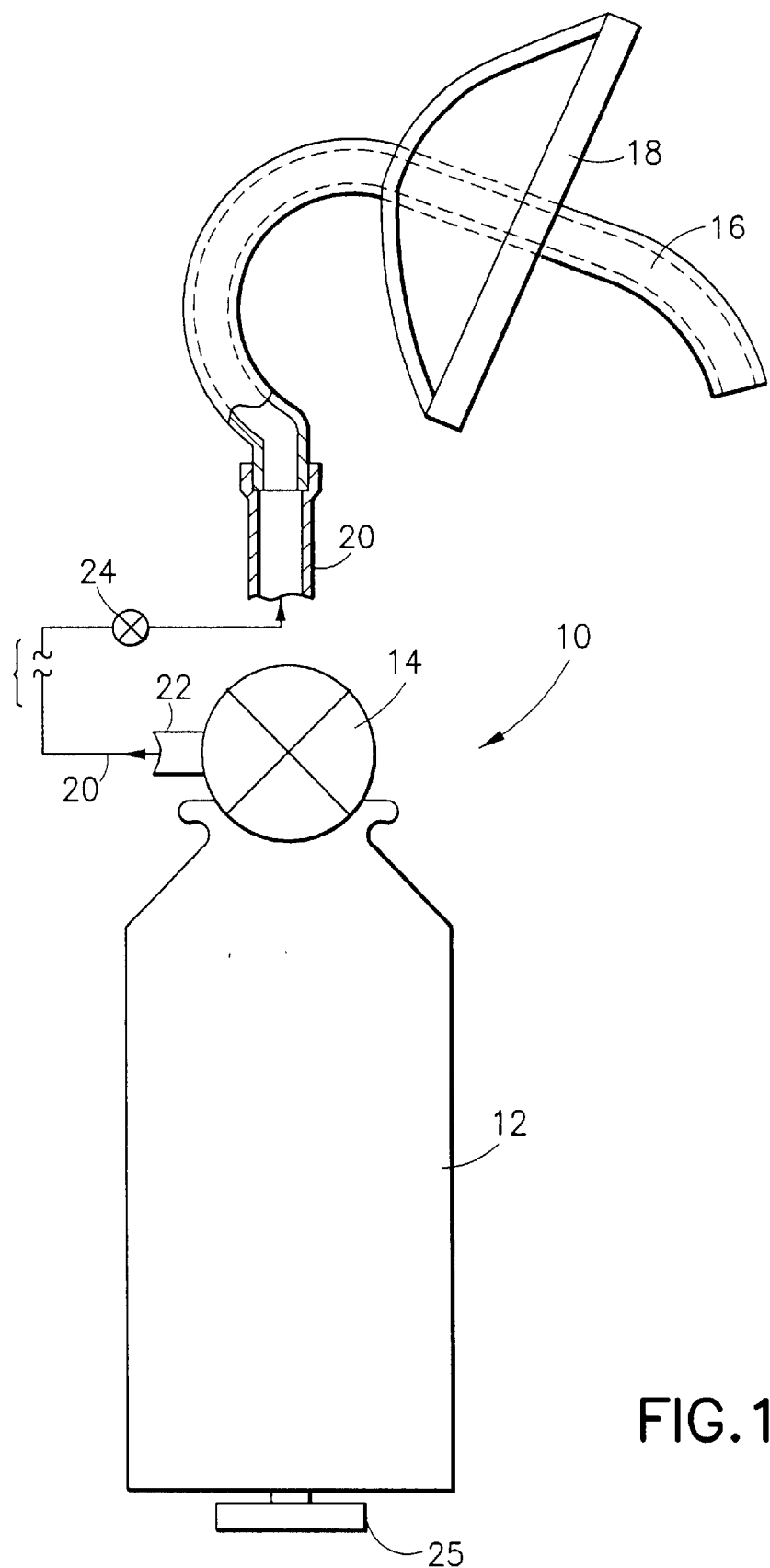
FIG. 1 is a schematic of the apparatus of the invention.

In accordance with the invention and as shown in FIG. 1, the device, generally referred to as 10, comprises broadly: an evacuated canister 12, a puncture member, generally designated as 14, disposed in the opening 26 of the canister 12, and a hollow tongue depressor 16 having mounted thereon a sealing mask 18, which mask 18 is designed so as to seal the victim's oral and nasal passages (not shown) upon application of the mask to the victim. Suitable conduit means 20 connect at one end to the outlet 22 of the puncture member 14 and at the other end to the tongue depressor 16. Disposed in the conduit means 20, intermediate the canister 12 and the tongue depressor 16 is a release valve 24; the function of the release valve 24 when in an open position being to provide a through conduit from the oral cavity (not shown) of the victim to the interior of the evacuated canister and thereby create a low pressure zone in the oral cavity above the lodged bolus by having a significant portion of the air above the bolus evacuated to the interior of the canister through pressure equalization. A pressure indicating means 25 may be connected to the interior of the canister 12 to show the degree of evacuation of the canister 12.

Figure 2:
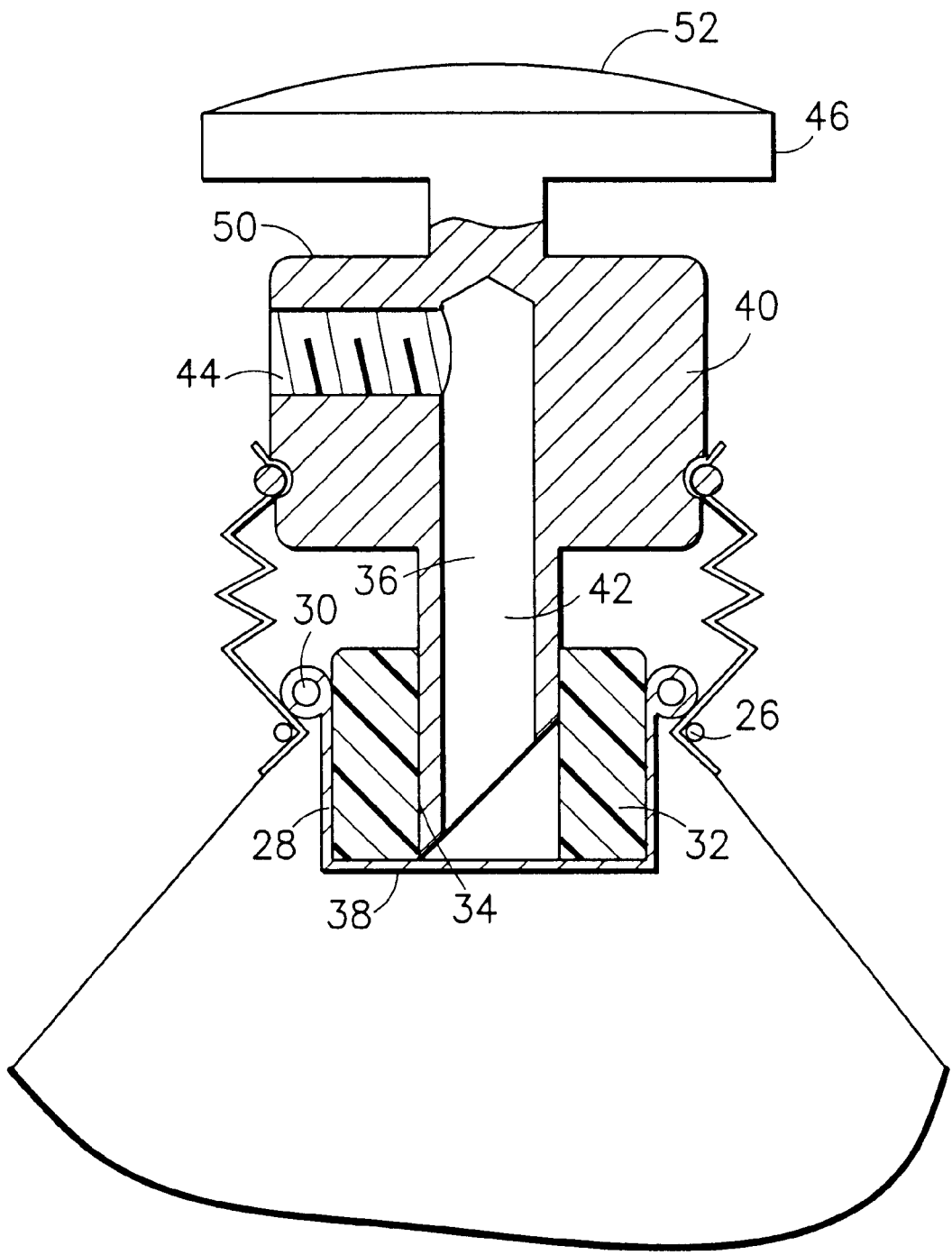
FIG. 2 is a partial section of a release valve disposed in the neck of the canister.

FIG. 2 shows an embodiment of the puncture member 14 connected to the canister 12 at the neck opening 26. A thin-walled, puncturable cup-like member 28 is seam rolled in a conventional manner to the bead 30 of the canister 12. Disposed within and frictionally fitted within the cup-like member 28 is a guide 32 having a central opening 34 adapted to receive the puncture member, generally designated as 14. The puncture member 14 has a hollow shaft 37 having a central opening 36, the leading edge of the hollow shaft 37 being tapered at a 45° angle to provide a puncturing edge 39 for the shaft 37, which frictionally fits within the central opening 34 of the guide 32 and is advanced against the base 38 of the cup-like member 28. The opening 36 of the hollow shaft 37 extends at its end distal to the cup-like member 28 into and is integral with a body portion 40; the opening 36 in the hollow shaft 37 extending into and through the body portion 40 to a side opening 44. To aid in applying sufficient force to the puncture member 14 to rupture the base 38 of the cup-like member 28, a platform 46 is disposed above the body portion 40 through a shaft 48 extending from the top 50 of the body portion 40. A handle 52 may be affixed to the platform 46 by conventional means. Non-collapsible, flexible tube 54 is anchored to the bead 30 of the container 12 and to the puncture member 14 to isolate the hollow shaft 36 from the ambient surroundings, thus maintaining the vacuum and allowing flexing of the puncture member during the movement of puncture member 14 toward the base 38.

While a specific embodiment of a puncture member has been described, it will be apparent to those skilled in the art that other puncture structures may be utilized. What is essential is that the evacuated canister may be promptly and readily accessed while maintaining the isolation of the interior of the evacuated canister from ambient atmosphere.

To use the apparatus of this invention, the operator may insert the tongue depressor 16 into the oral cavity (not shown) of the victim and place the mask 18 against the victim's face so as to seal the oral and nasal cavities of the victim against the ambient environment. The puncture member 14 is forced against the cup-like member 28 to rupture the base 38 and thereby provide a communication between the interior of the canister 12 and the upstream side of the release valve 24. At this point, the release valve 24 is opened with the consequence that air is evacuated from the oral cavity and associated throat area above the lodged bolus thereby effecting an instantaneous and sustained pressure drop above the lodged bolus and a significant pressure differential on each side of the bolus which will overcome the forces of weight and frictional engagement between the bolus and the contiguous tissue against which the bolus is lodged and thereby move the bolus into the mouth for removal or other disposition.

Alternatively, the evacuated canister may be first punctured and then the tongue depressor and mask fitted to the victim; it being important that the release valve not be opened until such time that the tongue depressor and mask are in place.

Figure 7:
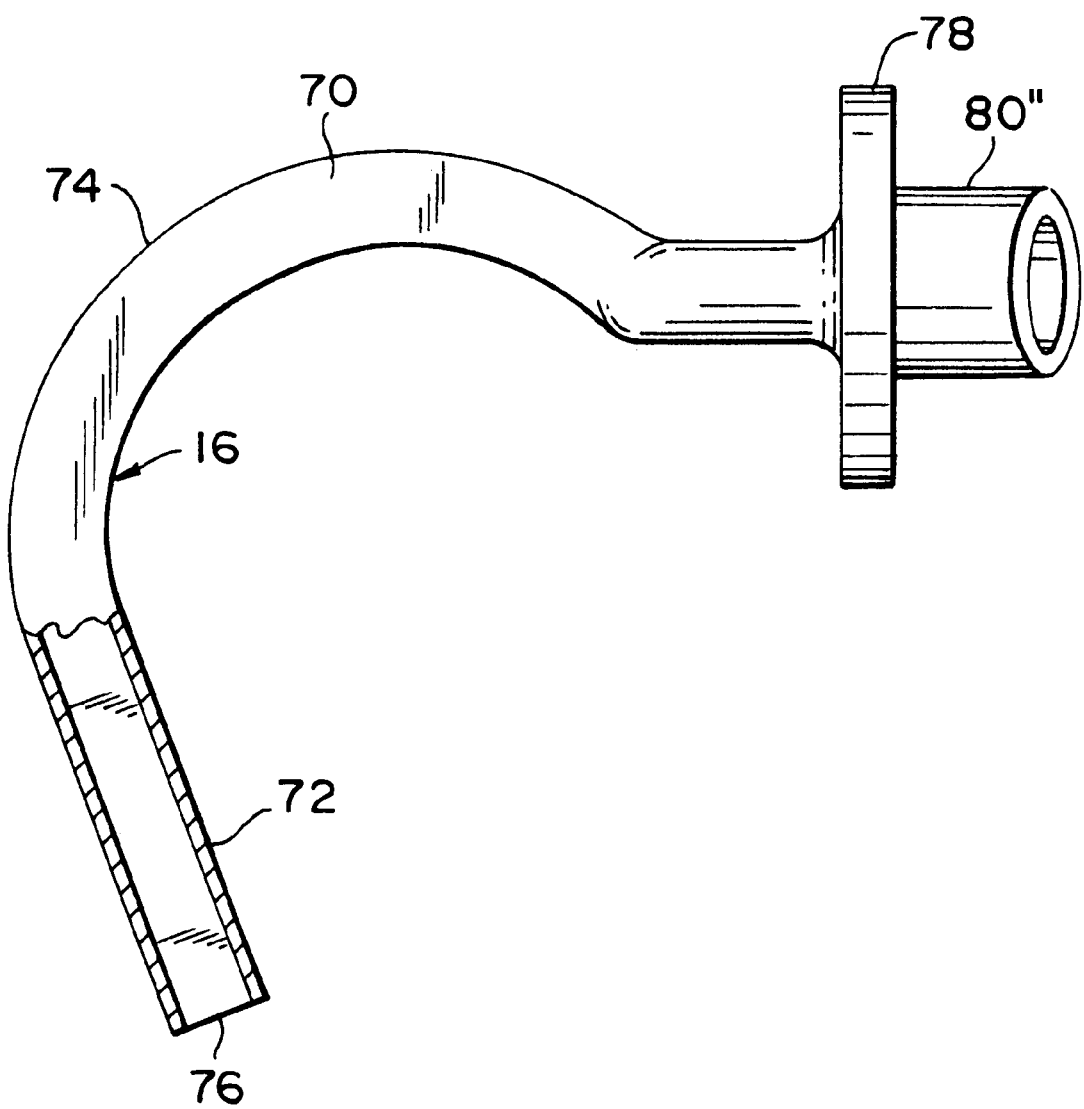
FIG. 7 is a cross section of the preferred embodiment of the tongue depressor.

The preferred embodiment of the tongue depressor, as shown in FIG. 7, is described hereafter. As shown in FIG. 1, the apparatus of this invention includes a hollow tongue depressor 16. In FIG. 7, the tongue depressor is generally designated as 16. The tongue depressor 16 comprises a hollow, rectangularly shaped member 70 having a substantially straight, open-end portion 72 for insertion into the posterior pharynx zone of a human, a curvilinear portion 74 extending from the terminus of the open-end portion 72, distal to the open-end 76, to the lip engaging annular flange portion 78, and a tubular portion 80, extending beyond the annular flange portion 78, which tubular portion is designed to attach to the conduit means 20 of FIG. 1. The annular flange 76 may form a portion of the mask 18 (not shown) of FIG. 1, which mask seals the oral and nasal cavity of the victim.

To properly position the tongue depressor within the posterior pharynx zone of an adult, the length of the tongue depressor from the open-end 76 side of the annular flange 78 to the open-end 76 is 16.5 centimeters. The dimension of the rectangular-shaped member is two (2) centimeters by one (1) centimeter.

The tongue depressor controls the holding of the tongue to the floor of the mouth by pressing the two (2) centimeter surface against the tongue. The substantially straight portion 72 permits the open-end 76 to be disposed above the site of the obstruction and posterior to the epiglottis.

The apparatus of this invention was tested under various operating conditions (Tests No. 1–3). The results are hereafter presented and discussed.

Figure 4:
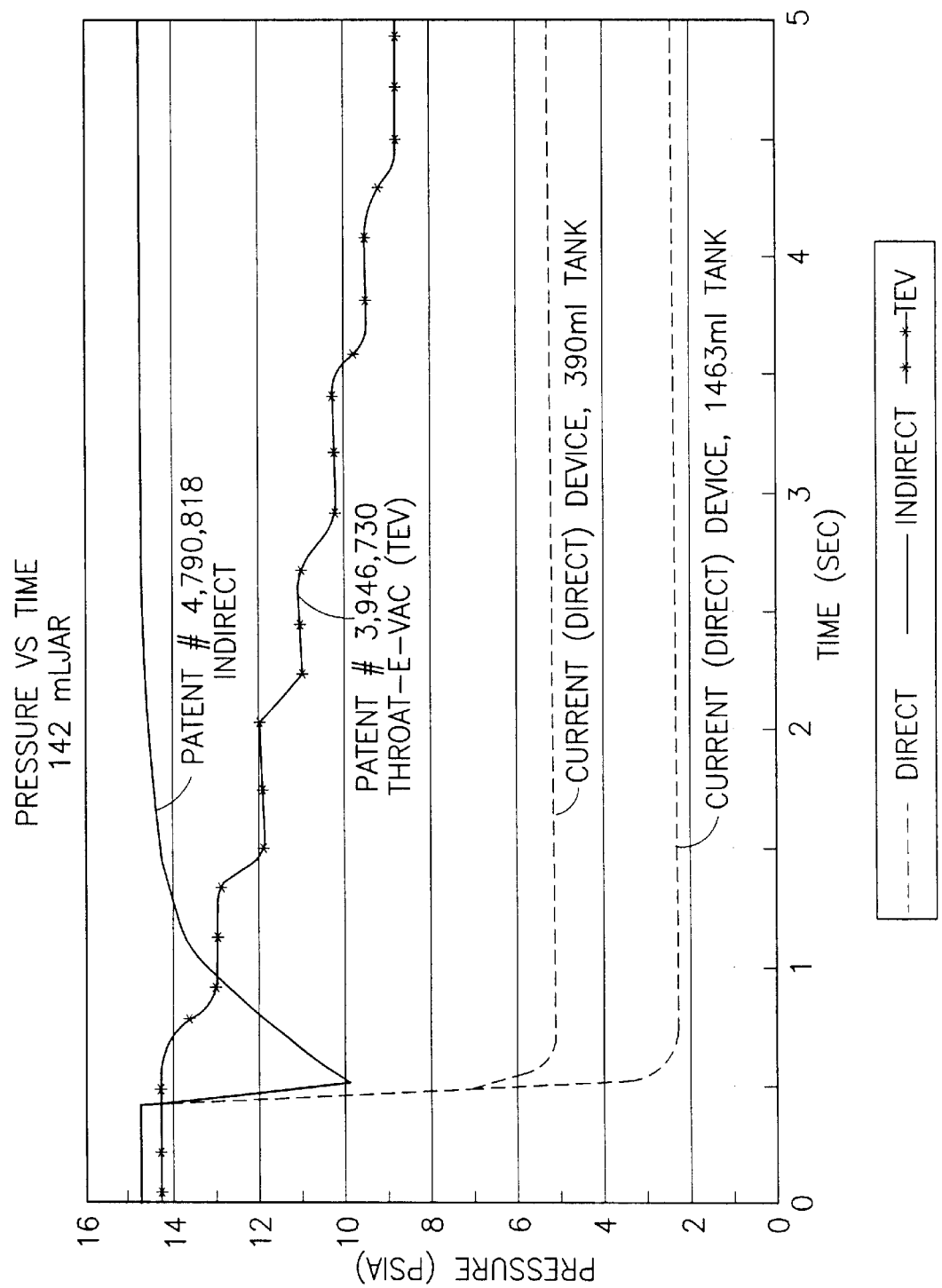
FIG. 4 is a graph comparing the apparatus of this invention with prior art devices.

Test No. 1 shows the degree of vacuum (pressure differential) that can be produced in the oral cavity for the devices of this invention, the device of the DeLuca patent and the device of the Neward patent. Prior to the test, the device of this invention was pre-evacuated to about one psi and DeLuca's device was pressurized up to 200 psi. The Neward device is a hand-pump evacuation apparatus. A 142 ml plastic jar was used to simulate the mouth cavity. The results are shown in FIG. 4 as vacuum pressure versus time. It can be seen from FIG. 4 that the device of this invention can produce as much as a 12 psi vacuum pressure drop, while the DeLuca device produces only about a momentary 5 psi pressure drop in the oral cavity and the Neward device a 6 psi drop over time. Also, and unexpectedly, note that for the device of this invention, the reduced pressure is sustained over a protracted period. Therefore, with regard to favorable dislodgement conditions 1 and 2, mentioned above, the device of this invention is clearly superior to the DeLuca device.

Even though the Neward device shows the capability of producing a greater vacuum pressure differential than the DeLuca device, the Neward apparatus and process is time consuming and gradual and, accordingly, it does not meet the dislodgement condition 3 mentioned above. Further, it is again noted that for manual techniques, such as back slapping or the Heimlich maneuver, the pressure differential created across the object is on the order of 0.5 psi. Consequently, the device of the invention will be quite useful for situations where the required pressure differential for the removal of the lodged object substantially exceeds the capability of the manual techniques.

Figure 3:
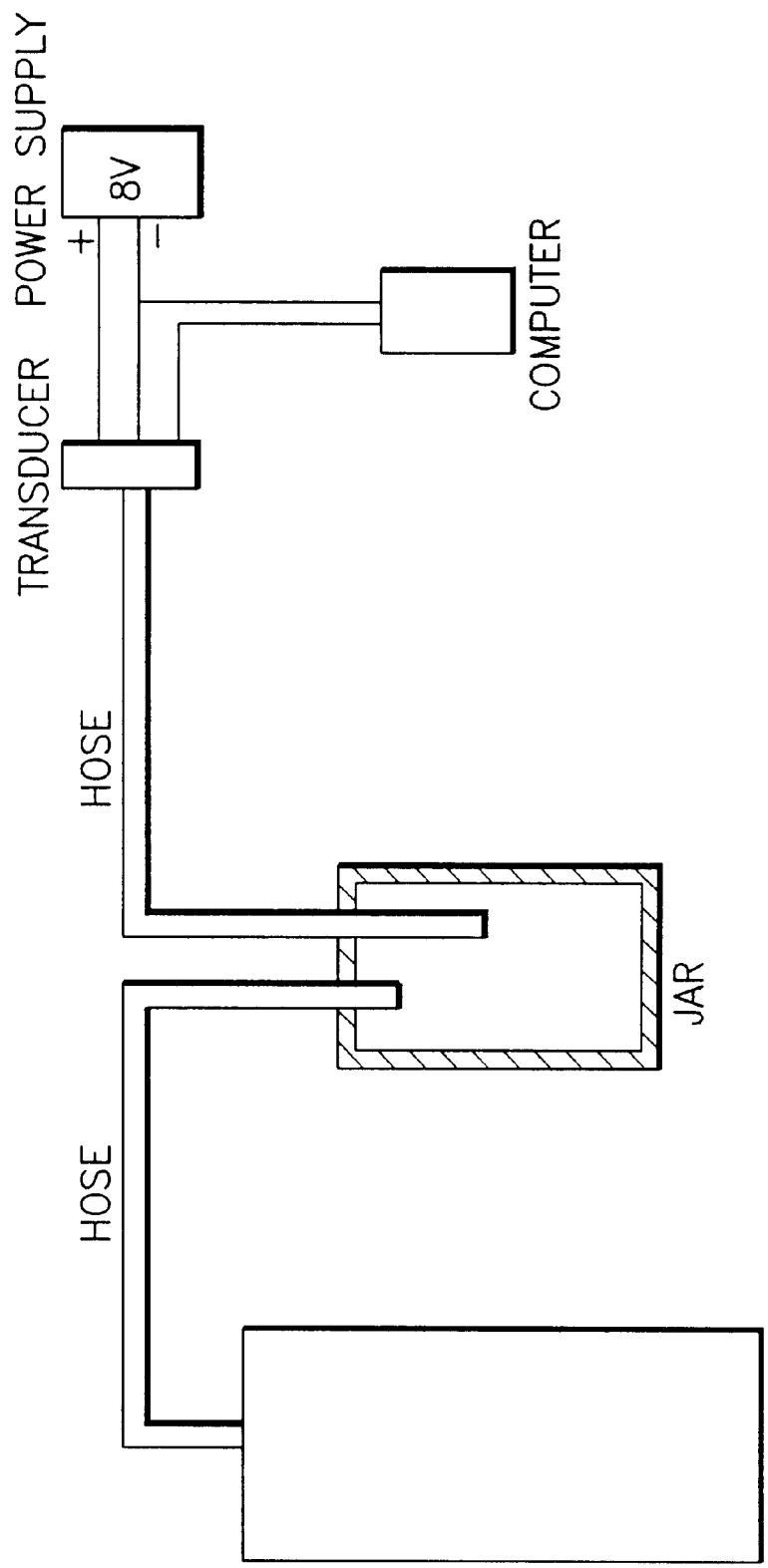
FIG. 3 is a schematic of the test model apparatus used to obtain the data of FIG. 4.

A schematic of the experimental equipment is set forth in FIG. 3.

Figure 6:
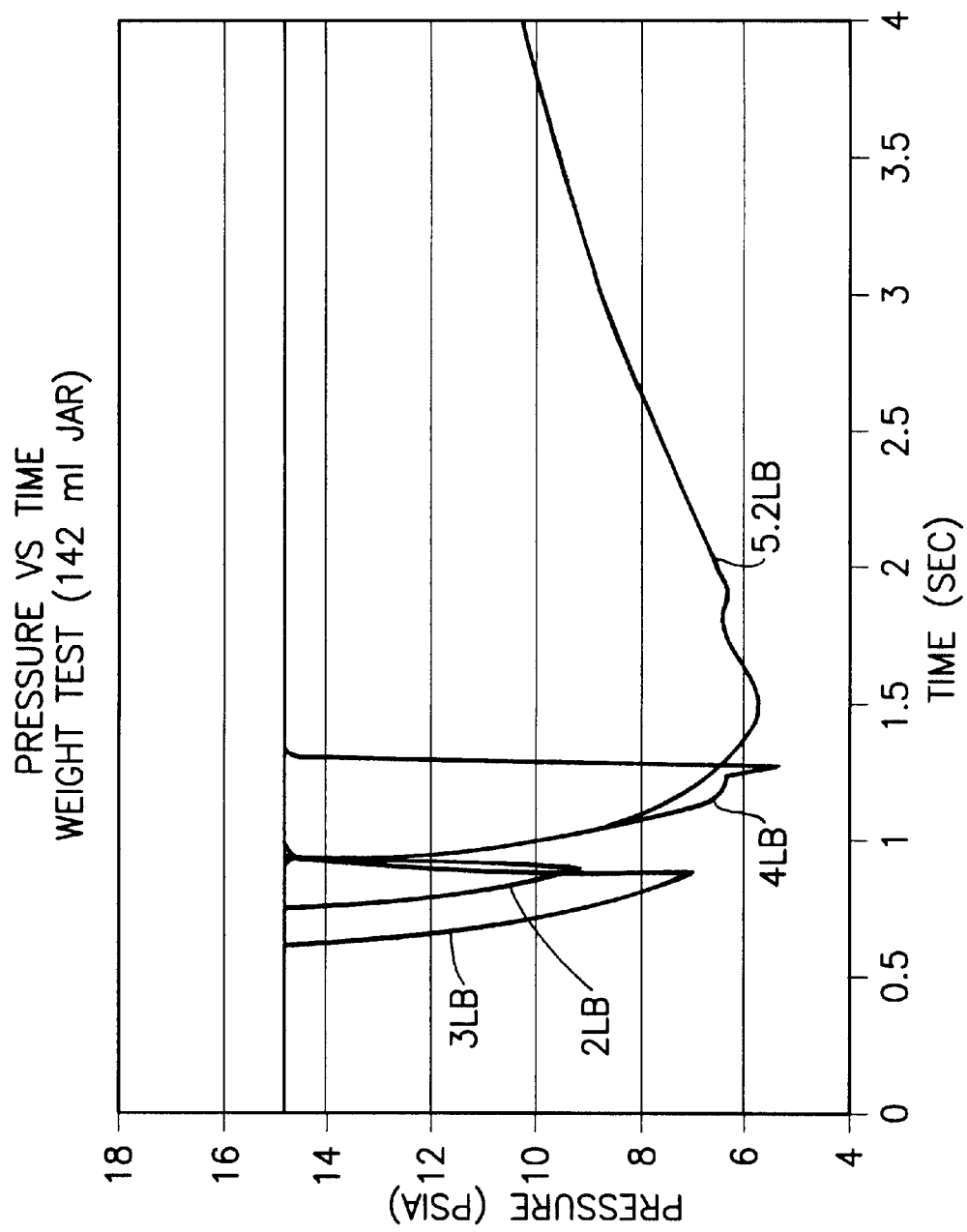
FIG. 6 is a graph plotting the pressure against time for various weights.

Test No. 2 measures the maximum upward force that the device of this invention will exert on the lodged object. In this test, the 142 ml plastic jar was modified by addition of a ¾ inch diameter pipe to the bottom of the jar to simulate the human airway. Different weights were tested and the results are shown in FIG. 6. The maximum weight lifted by the device was 5.2 lbs, which should be quite sufficient to remove the obstructing object from the airway.

Figure 5:
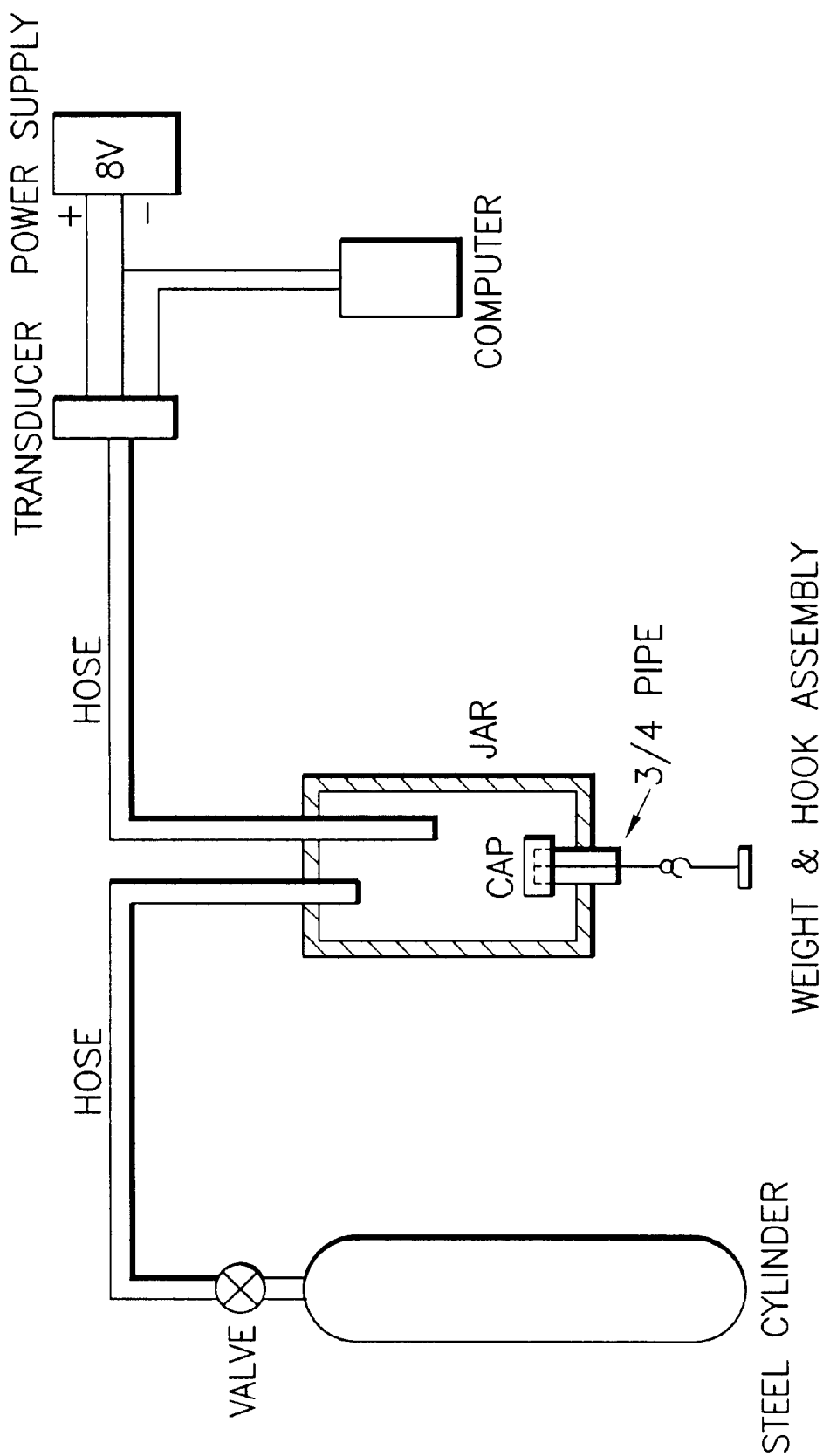
FIG. 5 is a schematic of the test model apparatus used to obtain the data of FIG. 6.

A schematic of the testing equipment for Test No. 2 is shown in FIG. 5.

Test No. 3 was carried out to determine if the device of this invention will remove a piece of frankfurter lodged in a simulated airway using a dummy and a face mask. In this test, the frankfurter piece placed inside the ¾-inch-diameter pipe created a complete blockage. A hose then was connected from the mouth of the dummy through its head to the jar. The face mask was placed over the dummy's mouth and nose and the release valve was opened. Instantly, the frankfurter piece flew out of the pipe.

While the present invention has been described by way of preferred embodiment, it is to be understood that this description is for illustration purposes only and the invention should not be limited thereto, but only by the scope of the following claims.

We claim:

1. A method of removing a mass lodged in the pharynx and/or larynx cavity of an animal air passage comprising the steps of:

(a) sealing the nasal and oral cavities and depressing the tongue of the animal; and (b) communicating an evacuated canister and the sealed oral cavity to thereby create a lower pressure in the oral cavity downstream of the lodged mass.

2. The method of claim 1, and further wherein the canister is valved.

3. The method of claim 1 or 2, and further wherein the animal is a human being.

4. A method for removing a mass lodged in the pharynx and/or larynx of an animal air passage comprising the steps of:

(a) sealing the nasal and oral cavities while depressing the tongue of the animal;

(b) providing a means of communicating a valved and sealed evacuated canister and the sealed animal air passage;

(c) unsealing the valved evacuated canister, and (d) communicating the evacuated canister and the unsealed animal air passage through opening the valve.

5. The method of claim 4, wherein the evacuated canister is unsealed and subsequently the nasal and oral cavities are sealed.

6. The method of claim 4, wherein the nasal and oral cavity and the tongue of the victim is first sealed, and subsequently the sealed evacuated canister is punctured.

* * * * *